US005617155A

United States Patent [19]
Ducarouge et al.

[11] Patent Number: 5,617,155
[45] Date of Patent: Apr. 1, 1997

[54] METHOD FOR DETERMINING MEASUREMENT PARAMETERS FOR A SPECTACLE WEARER

[75] Inventors: Christian Ducarouge; Richard Grisel; Nicholas Giraud, all of Lyons; Helene Sottocasa, Verrieres; Alain Chansavoir, Saint-Maur; Ahmed Haddadi, Draveil, all of France

[73] Assignee: Essilor International, France

[21] Appl. No.: 429,971

[22] Filed: Apr. 27, 1995

[30] Foreign Application Priority Data

May 3, 1994 [FR] France .................. 94 05400

[51] Int. Cl.$^6$ .................. A61B 3/10; A61B 3/00
[52] U.S. Cl. .................. 351/204; 351/200
[58] Field of Search .................. 351/204, 200, 351/246; 33/200; 356/124, 127; 364/560

[56] References Cited

U.S. PATENT DOCUMENTS 4,591,246  5/1986  Cousyn .................. 351/204
4,762,407  8/1988  Anger et al. .................. 351/204
5,450,335  9/1995  Kikuchi .................. 364/560

FOREIGN PATENT DOCUMENTS 2620927   3/1989   France .
2690832  11/1993   France .
8812095  11/1988   Germany .

Primary Examiner—Hung X. Dang
Attorney, Agent, or Firm—Fish & Richardson, P.C.

[57] ABSTRACT

A method for determining measurement parameters from the image of a spectacle wearer wearing a spectacle frame is disclosed in which the position of the center of the pupil of each eye is obtained automatically by analyzing the luminance gradient in the region of the pupils and the positions of the horizontal and vertical straight lines tangential to the frame are also obtained automatically by luminance gradient analysis and extraction of the contours of the frame, enabling said parameters to be calculated accurately.

20 Claims, 4 Drawing Sheets

METHOD FOR DETERMINING MEASUREMENT PARAMETERS FOR A SPECTACLE WEARER

BACKGROUND OF THE INVENTION

The present invention relates to the field of optics and specifically to the field of optical metrology, and more precisely to the measurement of the various parameters needed to produce spectacles. In the production of spectacles, it is necessary to cut the lenses designed to be fitted into the frame as a function of the choice of frame and of various parameters linked to the spectacle wearer. These parameters include the distance between the pupils or in other words the horizontal distance between the eyes of the spectacle wearer, and various heights or distances with respect to the pupil of each eye.

Various optical metrology methods are known. Conventionally, the optician directly measures the various parameters on the spectacle wearer, using a measuring instrument. This method is not very accurate. Another disadvantage is that the measurements are not taken in the natural position for the spectacle wearer, but rather at a position for which the spectacle wearer is somewhat constrained, with his head being kept at a fixed position, various measuring devices being present in the visual field, etc.

To overcome these disadvantages, in French Patent Application 2,690,832 an image of the face of the wearer carrying a frame is captured by means of a digitizing device, the various parameters then being measured on this image. It is suggested there that this image be displayed on a screen. Following this, the optician uses a mouse pointing device to locate the extreme upper and lower, and lateral, points of the frame on the screen to thereby trace a rectangular framework tangential to the frame, on the screen. A comparison between the dimensions of this framework and the theoretical shape of the frame obtained by other means, enables the image to be scaled to a known size. Following this, the position of the pupil of each eye is marked on the image, in order to calculate the various parameters.

A similar method is implemented in a device known as the Video-Infral marketed by the Carl Zeiss company. Using two video cameras and a mirror, front and side views are obtained of the spectacle wearer. The optician then uses a mouse pointing device to trace, on these images, the tangents to the frame, and then moves the cursor or the mouse in order to determine the position of the center of the eye. The position of the patient's pupils with respect to the frame is then measured on the front view of the wearer, and the inclination of the frame with respect to the vertical is located on the side view image.

In both procedures, the optician is required to trace various points of the frame with the mouse, and to visually ensure the tangents are parallel. This renders these procedures time-consuming in practice. Moreover, the line drawing operations reduce the accuracy of measurement; evaluation of tangency between the frameworks and the spectacle frame depends on the person operating the device. It is difficult for these procedures to furnish reproducible results when successive measurements are taken.

In a device marketed by Rodenstock under the name Videocom, is proposed to employ a simple video camera to obtain an image of the person wearing the frame after a millimetric scaled accessory has been fitted onto said frame. Measurement is then done by clicking at the desired points of the image on the screen. Measurement in this device thus lacks accuracy.

SUMMARY OF THE INVENTION

The present invention enables these disadvantages to be overcome. It provides reproducible, reliable and operator-independent measurements. It enables intervention on the part of the operator to be limited. It can be completely automated and supplies accurate measurements regardless of the frame chosen.

The invention is particularly useful for implementation with the device described in French patent application 2,690,833 marketed by the assignee under the name Videocentron.

The invention provides a method for determining measurement parameters for a spectacle wearer from an image of said spectacle wearer provided with a spectacle frame comprising the steps of determining, on said image, the position of the horizontal and vertical straight lines tangential to said frame and the position of the centers of the pupils of the eyes of said wearer and calculating the values of said measurement parameters from said positions,
and including the steps of:
automatically determining, on said image, the position of the center of each pupil by analysing the luminance gradient in the region of each pupil, and determining automatically, on said image, the positions of the horizontal and vertical straight lines tangential to said frame, by luminance gradient analysis and extraction of the contours of said frame.

The invention limits human interventions, and provides reproducible results.

In a preferred embodiment, the positions of the horizontal and vertical straight lines tangential to the inside contour of that are determined in the image on each half-frame.

This method is more accurate than the known way of seeking the tangents to the spectacle frame on the image.

The step consisting of determining the position of the center of each pupil of the eye automatically on said image preferably comprises the steps consisting, for each pupil, of:
determining a window covering the region of the pupil;
determining, within said window, those point on the image having a luminance that is higher than a threshold value;
calculating the position of the centroid of said points.

In this case the step consisting in determining said window is done by seeking, in the region of each pupil, that point in the image for which the norm of the gradient is a maximum, and then centering a window of a predetermined size on said point.

The use of such windows enables the method to be carried out more quickly.

The method may include a step consisting in defining four windows of predetermined size around the position of the center of each pupil, each containing one straight line tangential to the inside contour of each half-frame.

The use of such windows enables the method to be carried out more quickly without the need to seek a tangent in each window.

The step consisting in determining the positions of the horizontal and vertical straight lines tangential to said frame automatically can comprise the steps, within each of said windows, of:
determining, within said window, those points on the image for which the norm of the luminance gradient is higher than the threshold value in order to obtain the inside and outside contours of the spectacle frame within said window;

determining the shape of said frame within said window, from said contours;

determining, as a function of said window, the tangent to the inside contour of said frame Advantageously, said threshold value is selected whereby a predetermined number of said points on the image have a value of the norm of their luminance gradient above said threshold value.

Angles of inclination can be calculated from the image, the method then comprising the steps of:

supplying at least a real contour of said frame;

calculating, for the various possible values of angles of inclination, the projection of said real contour on said image;

comparing said projection with the contours extracted from said image by calculating, for said values of angles of inclination, the correlation between said projection and said contours extracted from said image;

the values of said angles of inclination being those values for which said correlation is at a maximum.

When the angles of inclination are known, the method can comprise the steps of:

supplying at least a real contour of the spectacle frame, and the angles of inclination of said frame;

calculating, as a function of said angles of inclination, the projection of said real contour on said image;

comparing said projection with the contours extracted from said image by sweeping said projection over said image and calculating therefrom, for each position of said projection, the correlation between said projection and said contours extracted from said image;

determining the positions of the horizontal and vertical straight lines tangential to said frame, using the position of said projection for which said correlation is at a maximum.

In one preferred embodiment, the step consisting in calculating the values of said measurement parameters from said positions is achieved by comparing the relative positions of the centers of the pupils of the eyes of the spectacle wearer and the straight lines tangential to the inside contours of said frame.

Further characteristics and advantages of the invention will become more clear from the description that follows of embodiments of the invention provided simply by way of non-limiting example with reference to the attached drawings.

DETAILED DESCRIPTION OF PREFERRED EMBODIMENTS

Figure 1:
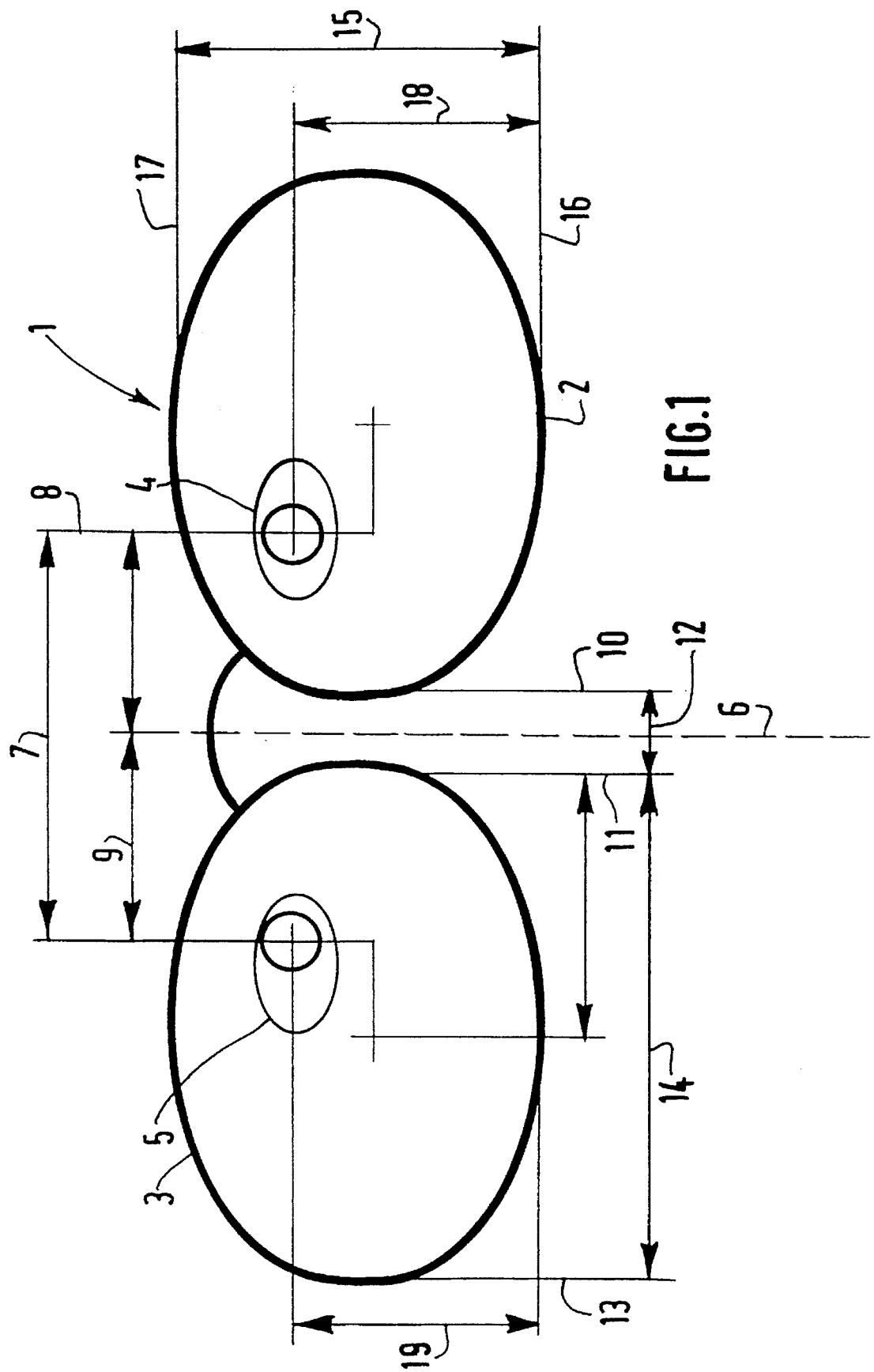
FIG. 1 shows diagrammatically the various measurement parameter for a spectacle wearer.

FIG. 1 shows diagrammatically the various measurement parameters for a spectacle wearer. On FIG. 1 there can be seen a spectacle frame 1 comprising a left-hand half-frame 2 and a right-half frame 3, the spectacle wearer's left eye 4 and right eye 5 being shown diagrammatically. In order to prepare the spectacle glasses or lenses that suit the spectacle wearer and the chosen frame, it is necessary to know the internal shape of the frame in order to cut the glass. It is also necessary to know the position of the wearer's eyes with respect to the frame. The following parameters are currently used: The first is the distance between the centers of the two eyes of the patient which is equal to the sum of a right hand offset and a left hand offset respectively corresponding to the horizontal distances between the right hand pupil and the axis of the nose and between the axis of the nose and the left hand pupil. On FIG. 1, the dashed line 6 represents the axis of the nose, the dimension 7 is the distance between the pupils and the dimensions 9 and 8 are the two right hand and left hand offsets. The distance between the two vertical straight lines (10, 11) tangential to the inside of each half-frame at the nose side is called the bridge. The dimension 12 in FIG. 1 corresponds to the bridge. The width of each half-frame, in other words the distance between the two vertical straight lines 11 and 13 tangential to the inside of each half-frame is called the A distance (dimension 14) and the distance between the two horizontal straight lines 16 and 17 tangential to the inside of each half-frame is called the B distance (dimension 15). The intersection between the center line of the two horizontal tangential straight lines and the center line of the two vertical tangential straight lines is called the center of each half-frame. The distance between the center of the pupil of the left hand eye 4 (or, respectively, the right hand eye 5) and the horizontal straight line 16 tangential to the bottom of the inside of the left hand 2 (or, respectively, right hand 3) half-frame is called the left hand height 18 (or, respectively, right hand height 19). The horizontal or vertical distance between the center of each half-frame and the center of the pupil of the corresponding eye is called the horizontal or vertical, left hand or right hand, off-axis distance. The vertical distance between the center of the (right hand or left hand) pupil and the inside periphery of the frame below the center of the pupil is called the (right hand or left hand) depth of the frame below the pupil. The maximum distance between the center of the (right hand or left hand) pupil and the inner periphery of the corresponding frame portion is called the maximum (right hand or left hand) radius. The maximum radius enables one to determine what is the minimum diameter of lens that can be used.

The aim of the invention is to measure these various parameters from an image of a spectacle wearer provided with a frame. This image is advantageously an image obtained by a video camera coupled to a digitizing board; such an image can for example be supplied by the Videocentron device mentioned above. It can also be obtained by means of a digital camera, a scanner or any other means. Such an image is scaled in a known manner, for example, due to the presence of a scale of a known size inside the image, or any other means enabling the magnification factor of the image (knowing the focal length, etc.) to be determined.

The image is a color or gray scale digital image on which the face of the patient and the frame appear. On this image, a reflection from the cornea of each eye can also be seen when the spectacle wearer is looking at a light source.

The expression "image" should be taken here to mean a matrix of numbers consisting of a set of points or pixels. In the case of an image obtained from a video camera, it is the luminance or any other digital representation of the image (hue saturation intensity (HSI) or red green blue (RGB)) that is operated on.

The expression "gradient" should be taken to mean the usual mathematical function in its known application to discrete images. In place of a gradient, it is also possible to employ any function that represents variations in a numerical field, such as for example the Laplace function.

The term norm should be taken to means the classical norm of Euclidian geometry. Any other norm could be used or even a function which is not a norm in the mathematical sense of the term, such as for example a simple sum of the absolute values of components, or yet again the square of the Euclidian norm.

The terms x-axis and y-axis are used conventionally for the horizontal and vertical coordinates.

Figure 2:
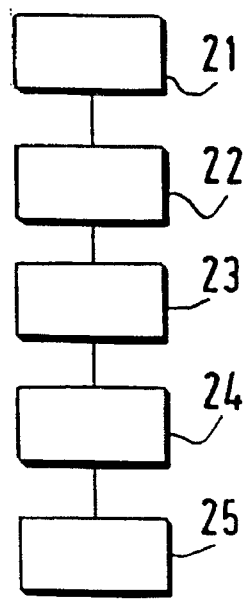
FIG. 2 is a flow chart of the various steps in the determination of the position of the center of each of the wearer's pupils on the image.

FIG. 2 is a flow chart showing the various stages in determining the position of the center of each pupil of a spectacle wearer, on the image. According to the invention, the position of the center of each pupil is determined automatically by analysis of the luminance gradient of the image. Firstly, the reflection of the cornea is detected automatically by calculating the pixel having the maximum luminance gradient norm. After applying a threshold value to the luminance information, the center of reflection is then determined by calculation of the weighted center. Calculation can be done successively on each pupil, or in parallel. The invention will be described with reference to FIG. 2 for one eye.

In the flow chart in FIG. 2 a window inside of which the center of the pupil will be sought is first determined at step 21. In a given apparatus, for a given position of the wearer of the frame, there is relatively little variation from one person to another in the position of an eye on the image. The detection window is located around the position intended for the eye and has a size that is determined experimentally for a given apparatus; its size is chosen so that the image of the eye is located in the window, regardless of the wearer.

The fact of using this window instead of working on the complete image enables the calculation time to be shortened, although it would also be possible to work on the complete image.

At step 22, the luminance gradient norm is determined at every point, within the window determined at step 21.

At step 23, the boundary of the corneal reflection on the pupil, within the window, in other words the pixel having the maximum gradient norm is determined. A new, smaller, processing window is centered on this pixel. This window, for a given apparatus and a given position of the wearer of the spectacles, has a size determined experimentally in order to only comprise the reflection at the pupil. A smaller window is thus obtained. After this, the data is put into binary form, all pixels having a luminance value above a given level being put to one, and the remainder to zero.

At step 24, spurious reflections are eliminated by carrying out morphological thinning on the binary form of the window. This consists in comparing the value of a pixel of the image with the values of neighbouring pixels. Each pixel is assigned the minimum value found in a determined neighborhood of pixels. Thus, reflections of a size less than the neighborhood disappear.

At step 25, the centroid (ie that point the coordinates of which are the mean values of the coordinates of the set of pixels) of the adopted pixels is calculated, within the window of step 23. The point thus obtained is the center of the corneal reflection and corresponds to the center of the pupil concerned. It is also possible to calculate the weighted center of the pixels concerned using weighting factors corresponding to luminance values, without in this case first carrying out thresholding and binary value assignment.

At steps 21 to 25, the center of the second pupil is found by the same method.

One thus obtains the position of the center of each pupil of the spectacle wearer, in the image. When compared to known methods, the operator does not need to acquire the position of the wearer's pupil using a pointing device such as a mouse. The determination obtained is also more accurate than simple manual acquisition is. This thus provides automatic calculation of the distance between the pupils, by subtracting the x-axis coordinates of the centers determined.

Figure 3:
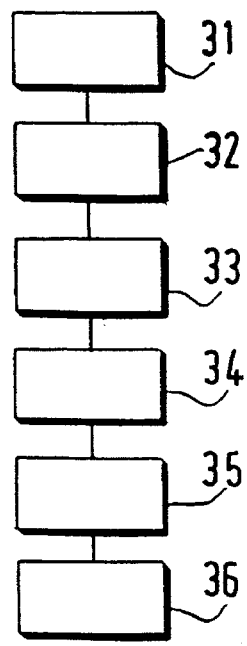
FIG. 3 is a flow chart of the various steps for determining the position of the vertical and horizontal tangents on the image.

FIG. 3 is a flow chart of the various stages for determining the position of the vertical and horizontal tangents on the image. According to the invention, the horizontal and vertical straight lines tangential to the inside of the frame are determined in a way that avoids the problems of the prior art related to the thickness of the frame and the interpretation of the colors of the frames.

The invention provides determination, on the image, of the inside and outside contours of the frame by luminance gradient analysis. The first stage is to calculate the luminance gradient norm at every point. Thresholding is then carried out, in other words the field thus obtained is put in binary form. In this way, the inner and outer contours of each half-frame are determined. The thresholding value can advantageously be determined by calculating the cumulative gradient histogram. The complete form of the frame is then determined by morphological fill-in. This then enables the inner tangent to the frame to be determined.

FIG. 3 is a more detailed flow chart of this part of the method according to the invention, for a half-frame. As was explained with reference to FIG. 2, calculation can be done successively on each half-frame, or in parallel. The invention will be described with reference to FIG. 3 for one half-frame.

At step 31, four processing windows (left hand, right hand, upper and lower) are determined, positioned with respect to the center of the pupil obtained as explained with reference to FIG. 2. Actually, in order to speed up digital processing, the position of tangents is determined in four processing windows and not on the complete image, as can be seen from the description accompanying FIG. 4. For a given apparatus and a given position of the spectacle wearer, the size and relative position of these four windows are determined experimentally so that each window may contain a tangent, for all shapes of frame. The four windows are arranged on the image with respect to the center of the pupil, which has already been determined.

At step 32, a map of the luminance gradient norm is calculated inside each window.

At step 33, a thresholding value is determined. This value can be a fixed value, experimentally determined by means of a given photographic apparatus; nevertheless, it can be advantageously determined by the following method. A cumulative histogram is calculated from the luminance gradient norm map: stated in other terms, for each possible value of the gradient norm, the number of pixels of the image for which the gradient norm has this value is calculated. This gives an idea of the distribution of the gradient norm over the image. A thresholding value is adopted such that a determined number of points have a gradient norm that is higher than said threshold. For example, in a 150×80 pixel window, a value of 2,000 pixels can be adopted. This number of pixels is the number of pixels constituting the contours of the frame.

At step 34, those points for which the gradient norm is higher than the threshold value from step 33 are selected. In each window, the inner and outer contours of the frame are thus obtained.

At step 35, more precise information on the contours obtained at step 34 is obtained by contour thinning. In this step, one direction is given priority in each window. Thus, in the two lateral windows, one is looking for the vertical tangent of the frame and thus the vertical direction is given priority; inversely, in the two upper and lower windows, it is a tangent horizontal to the frame that is being sought, and the priority direction is the horizontal direction. This will appear more clearly in the description accompanying FIG. 4. Thinning is carried out in a direction perpendicular to the priority direction within each window. This gives a more accurate image of the inner and outer contours of the frame. To take a specific example, if for example the left hand window is considered, thinning is carried out horizontally by for example comparing the norm for each pixel with the norm of its two neighbors in the horizontal sense, and only keeping the one for which the norm of its gradient is the highest.

In step 36, the contours obtained are put in binary form. A binary image is thus obtained which, in each window, contains the inner and outer contours of the frame.

Similar processing is carried out for each half-frame, either successively or in parallel, as described with reference to FIG. 2.

The binary image obtained at step 36 can either be processed directly or with the aid of a predetermined file specific to the frame. The relevant processing steps are described with reference to FIGS. 5 and 6.

Figure 4:
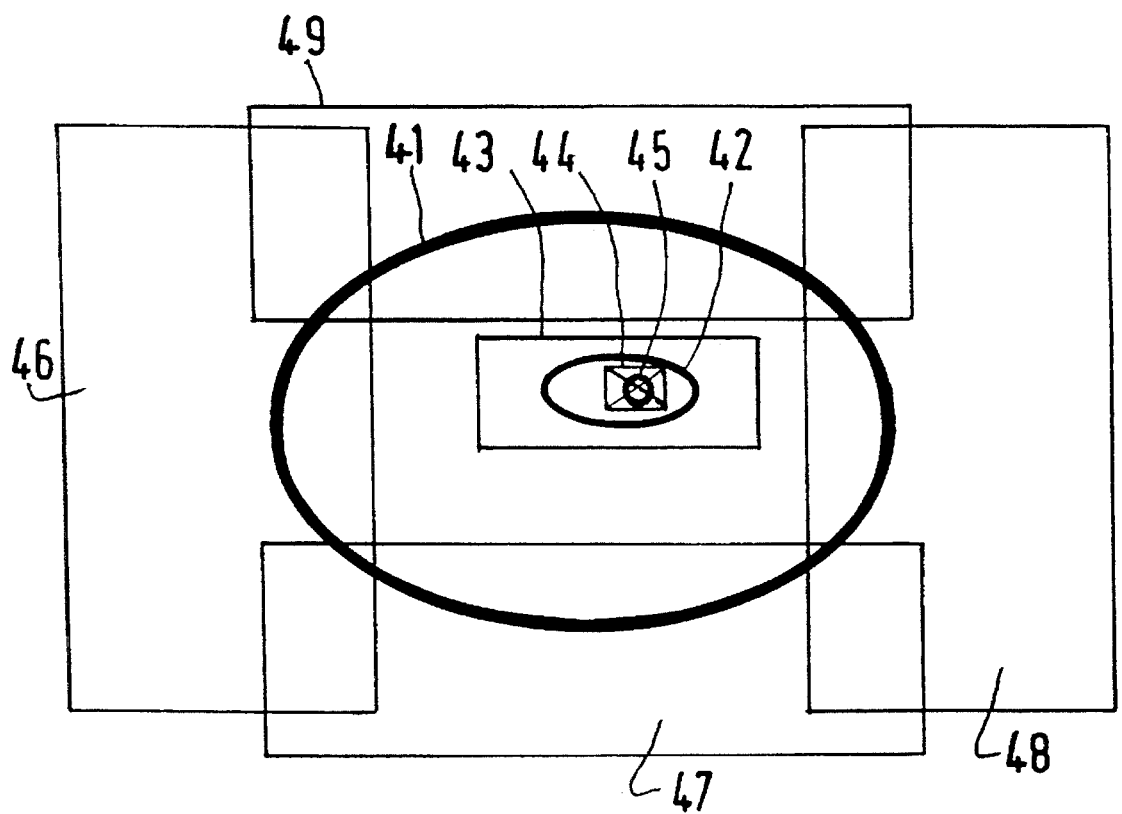
FIG. 4 is a diagrammatical view of the image of one half of a frame, with the processing windows.

FIG. 4 is a diagrammatical view of the image of a half-frame showing the processing windows described with reference to FIGS. 2 and 3. On FIG. 3, a half-frame 41 together with a diagrammatical representation of the eye 42 can be seen; 43 indicates the detection window for step 21 of FIG. 3; reference numeral 44 indicates the smaller detection window for step 24 of FIG. 2. Circle 45 is a diagrammatical representation of the contour of the pupil of the eye, or of the corneal reflection. Reference numerals 46 to 49 identify the four detection windows mentioned with reference to FIG. 3, within which the various tangents to the inside contour of the frame are sought.

Figure 5:
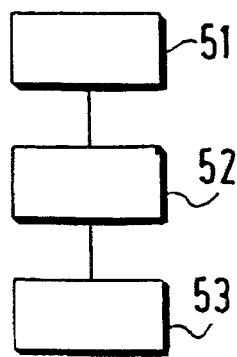
FIG. 5 illustrates a way of determining the horizontal and vertical tangents, according to the invention.

FIG. 5 shows one way of determining the horizontal and vertical tangents. Determination of the horizontal and vertical tangents should be taken here not to necessarily refer to determination of the line they follow but rather to determining their position within the image or simply with respect to the center of the pupil. Thus, determination of a horizontal tangent should be taken to mean determination of either the y-axis coordinate of this tangent, or, what amounts to the same thing, determination of the vertical distance between the tangent and the center of the pupil. In the method of determining the horizontal and vertical tangents of FIG. 5, no predetermined data file giving the shape of the frame is employed. As described above, steps 51 and 52 are carried out on each half-frame, in parallel or successively.

At step 51, the inner and outer contours obtained at step 36 are processed in each window in order to close the frame morphologically and thus fill in the parts of the frame between its inside and outside contour. Each window thus provides an image of the frame instead of simply its contours. Morphological fill-in is carried out by successive steps of expansion followed by thinning. In expansion, starting from the image of the contours, each pixel that is close to a pixel situated on one of said contours is given the value "black". Each contour is thus thickened. This step can optionally be repeated several times until the inner and outer contours meet. This is followed by a morphological thinning operation which reduces the size of the contours. This thinning operation is repeated if necessary the same number of times as the expansion operation. This provides an image of the frame. Morphological expansion and thinning can be done in a preferred direction within each window along the lines discussed with reference to step 35 in FIG. 3.

At step 52, a tangent to the inner contours is sought on the image of the frame in each window. The invention makes it possible to precisely find the straight line that is tangential to the inner contour. This is more accurate than the operator's visual evaluation employed in the prior art. To obtain the tangent, a straight line approximation method can for example be employed. This method consists in seeking the longest straight line segment within the frame in a given direction. Thus, using, for example, the upper window (reference numeral 49 on FIG. 4), a horizontal tangent is sought. Starting from the bottom of the window (in other words from the inner side of the frame) the length of the longest horizontal segment of the frame is determined, taking account of segments previously encountered and overlap. Where identical lengths are found, the segment that is the lowest, in other words in this example the one closest to the inside of the frame, is adopted. This gives the horizontal tangent to the inner contour of the frame.

It would also be possible to use another method for finding the tangent, such as for example a contour tracking method. Here, step 51 which is useful in the case of a straight line approximation method, could be S omitted. The tangents could be determined directly from the inner and outer contours. After step 52, the position of the horizontal and vertical straight lines tangential to the inside of each half-frame within the image and the position of the centers of the wearer's pupils are known. This enables the pixel values for the projection of the measurement parameters on the image to be provided. The depth of the frame below the pupil is calculated in pixels, using the point on the inside contour having the same position on the x-axis as the center of the pupil. Following this, the distance from the center of the pupil is calculated for all point on the inner contour of the frame and the maximum value for this distance is adopted as the maximum radius expressed in pixels. As the degree of magnification of the image is known, the values of the measurement parameters can be determined from their projection, in millimeters.

Then, knowing the angles of inclination of the frame with respect to the image, the various measurement parameters can be calculated. It should be remembered that the frame, as it is carried on a head that is free to move, may have slipped sideways, one side of the frame being higher than the other. The frame may also be offset with respect to the plane of the image, one side of the frame being more forward than the other: this happens when the person wearing the frame is not looking straight at the video camera or equivalent device, or slightly turns his head. Finally, the frame is not generally carried in a vertical plane. The angle between the plane of the frame and a vertical plane is called the pantoscopic angle. Knowing the value of these three angles and the value of the measurement parameters in their projection on the image, it is possible, at step 53, to calculate the values, in millimeters, of the measurement parameters: the A and B distances, the heights and the off-axis distances; knowing the distance between the pupils (see above in connection with FIG. 2), the bridge and the left and right hand offsets can be calculated. The depth of the frame below the pupil and the maximum radius are also calculated.

Figure 6:
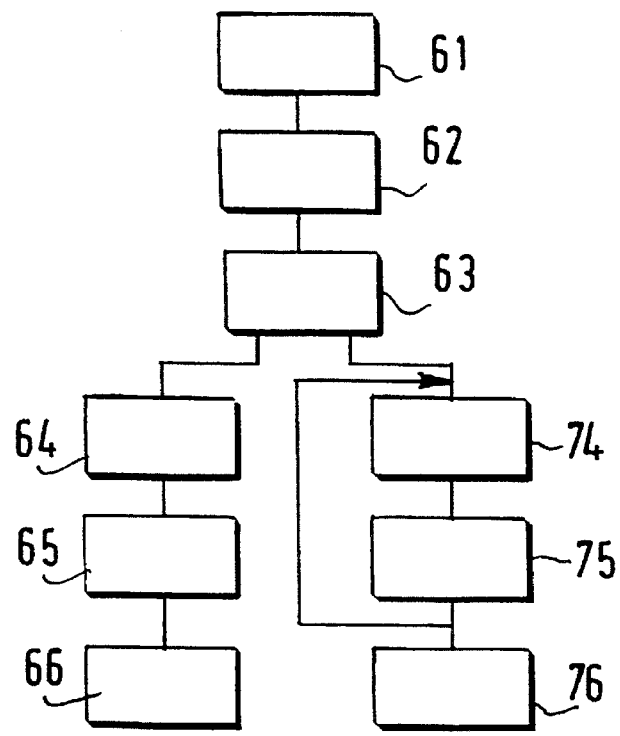
FIG. 6 shows another way of determining the horizontal and vertical tangents.

FIG. 6 shows another way of determining the horizontal and vertical tangents. In the embodiment of FIG. 6, an external data file representing the shape of the inner contour of the frame the spectacle wearer has chosen is employed in the image (true frame or true contours). A device for implementing this invention may for example be used for programming a file of this type. It can also be obtained by taking readings from a frame using a sensing device of the type available under the name Digiscan from the present assignee. The file can also be obtained by taking a video shot on a discriminating background or by any other means. Where this file provides the shape of the frame at the bottom of the lens-mounting groove, it can be corrected in order to obtain a file that represents the inner contour of the frame (for example by thinning inwardly by an amount equal to the depth of the lens mounting groove).

This file is used, according to the invention, for improving and speeding up calculation of tangents. This is achieved, in the invention, by aligning, through calculation, the actual contour of the frame with the image obtained, taking angles of inclination of the frame into account as well as the degree of magnification of the image. With the real contour superimposed on the frame obtained in the image, the tangents are calculated. After this, the geometrical parameters are calculated, taking account of the angles of inclination. Calculation of the tangents is simplified as the extreme points of the real contour of the frame are known accurately.

This part of the method makes it unnecessary to measure angles of inclination. It is in fact possible, using calculation, to simulate various angles of inclination on the real contour, for comparison with the frame obtained in the image. When there is maximum correlation between the real contour and the frame shown in the image, this gives the required angles of inclination.

FIG. 6 shows a detailed embodiment. As above, it is possible to work on each half-frame or on both half-frames simultaneously.

At step 61, the file representative of the frame is read. This can for example be a simple binary file. If necessary, the image in the file can be scaled up or down to match the magnification of the image.

At step 62, the shape of the frame is vectorized in order to reduce the number of points defining it, and simplify calculation. At step 62, any other data compression method could be employed, for example Bézier curve interpolation, or any other suitable function. This gives an image of the inside contour of the frame (real contour).

At step 63, thinning is applied to the real contour thus obtained in order to reduce acquisition errors, and make the internal contour of the frame more accurate. If necessary, the real contour is processed in order to yield the inner contour of the frame (to take account of the mounting groove).

Following this, various embodiments of the method can be followed. If the various angles of inclination are known, steps 64 to 66 can be followed. Otherwise, steps 74 to 76 can be followed.

At step 64, starting from the angles of inclination, the projection of the real contour of the frame onto the image is calculated. At step 65, the projection thus calculated is swept over the image. In other words, the projection of the real contour is shifted on the image and the correlation (overlap or number of common points) between the projection of the real contour of the frame, and the frame identified on the image is calculated at each position. When correlation is at a maximum, the position of the real contour gives the position of the frame.

At step 66, knowing the position of the frame, the positions of the various tangents are calculated. The position of the various tangents can be determined simply from a knowledge of the extreme points of the real contour (maxima on the x- and y-axes). If necessary, a straight line approximation method in the neighborhood of these points can be employed. In this case, a smaller window can be adopted for the approximation.

Following this, at step 53, the various measurement parameters: A distance, B distance, heights and distances with respect to the center of the pupils can be calculated; the bridge can be determined directly from the file supplying the frame, or the procedure described above can be employed.

Alternatively, if the various angles of inclination are not known, an iterative process can be followed (steps 74 to 76). At step 74, for given angles of inclination, the projection of the real contour of the frame onto the image is calculated. Then, at step 75, this projection is swept over the image and points of maximum correlation between the projection and the image of the frame obtained from step 36 are determined. This correlation value is stored in relation with the corresponding values for the angles of inclination. Step 74 is then repeated, after changing the angles of inclination. Iteration is continued until all the possible ranges of angles of inclination have been covered (for example for a tilt of between −3° and +3°, a pantoscopic angle between 0° and 15°, with sweeping being done in 0.5° steps, giving in all 13×31 iterations). When correlation is at a maximum, this indicates the correct values for the angles of inclination. Following this, the control passes to step 76.

At step 76, the procedure of step 66 is followed for calculating the measurement parameters. This gives the various parameters that need measuring.

The invention thus makes it possible to take account of the actual shape of each frame and, in particular, its thickness, and provides accurate and reproducible results. No intervention on the part of the operator is necessary. The method can be implemented with or without measurement of the angles of inclination.

Figure 7:
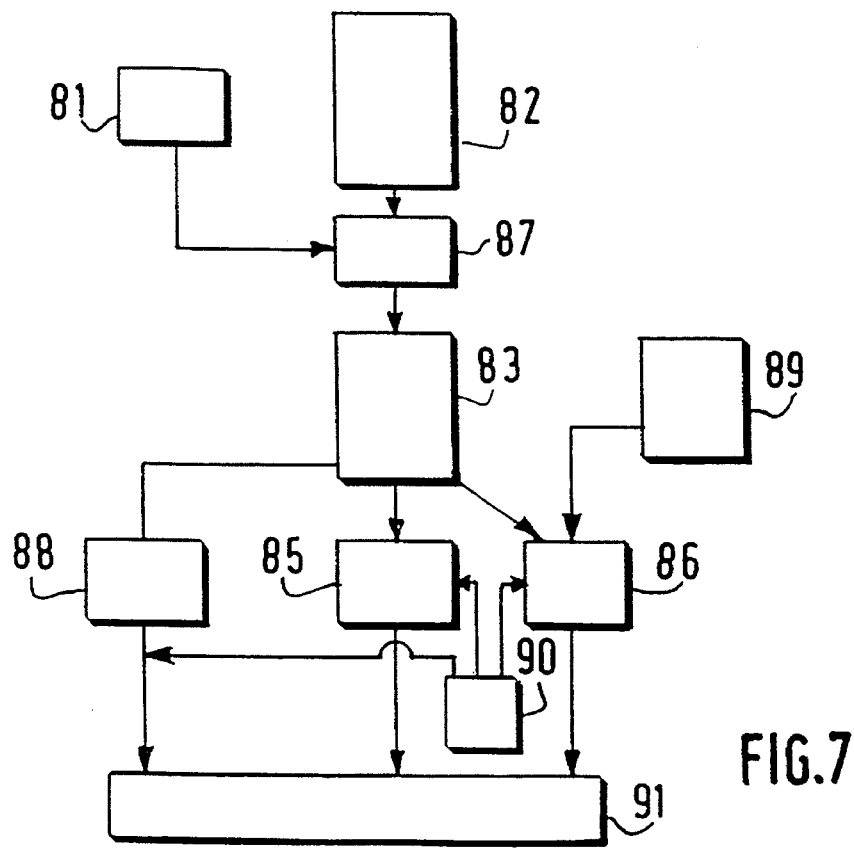
FIG. 7 is a flow chart illustrating another embodiment of the method.

FIG. 7 is a flow chart of another embodiment of the method. Here, the operator can personally intervene and make measurements on the image. These measurements are then compared with those obtained as described above. In FIG. 7, reference 82 is an overall representation of the various steps followed with reference to FIG. 2; reference numerals 83, 85 and 86 refer to the various steps described with reference, respectively, to FIGS. 3, 5 and 6.

At step 82, the position of the pupils of the spectacle wearer is determined on the image. The operator may optionally also determine this position, using a cursor or a mouse, as indicated by reference numeral 81. At step 87, the results are compared and the difference is displayed. Reference 88 indicates one way of manually acquiring the tangents to the frame, as is done in known devices. Reference 89 indicates the source of the external file containing the shape of the frame and reference 90 indicates a device supplying the angles of inclination. Reference numeral 91 indicates display of the geometrical parameters.

Various alternative embodiments can thus be applied to the invention: the method can be used in manual mode (81, 83, 88, 90 and 91), the operator or optician then having overall control. It can be used in automatic mode without prior knowledge of the frame (82, 83, 85, 90 and 91). It can also be used in automatic mode using an external file representing the frame. One can thus automatically determine angles of inclination (82, 83, 86, 89 and 91) or employ known values or values measured elsewhere (82, 83, 86, 89, 90 and 91).

The method makes it possible to take account of the three possible angles of inclination, and of the thickness of the frame. Simply by virtue of this fact, this invention provides results which are more reliable and more accurate than previous methods.

The method according to the invention can be implemented in any device able to supply an image of a person wearing a spectacle frame. It is particularly suitable for implementation in the device described in French Patent Application 2,690,833 mentioned above. The feature as described in that patent that are useful for implementing the method of this invention are incorporated herein by reference.

Obviously, the invention is not limited to the embodiments provided by way of example. One could thus determine the tangents with respect to the outer contours of the frame, or yet again with respect to the outline of the frame if this was needed by the optician. The use of processing windows speeds up calculation: this however is not indispensable to the performance of the method. In order to bring the image onto a known scale, it can be, if necessary, scaled up or scaled down. The angles of inclination could, if necessary, be calculated in another way, and for example, as described in French Patent Application 2,690,832. To determine the tangents, algorithms other than the straight line approximation methods could be employed, such as, for example, contour following methods. Above, analysis of the luminance gradient of the image has been described: any other way of representing the image (RGB, HSI) and/or any other type of mathematical operator (direct value of the pixel, Laplace function, etc.) could be employed. When analysing the real contour of the frame, although comparison on the basis of the inner contours of the frame has been described, it would of course be possible to use the outer contour of the frame or both the inner and outer contour.

What is claimed is:

1. A method for determining measurement parameters for a spectacle wearer comprising the steps of:

generating an image of a spectacle wearer provided with a spectacle frame;

determining automatically, on said image, by luminance gradient analysis, where a plurality of horizontal and vertical straight lines tangential to said frame would be positioned;

determining automatically, on said image, by luminance gradient analysis, where the center of each pupil of the eyes of said wearer would be positioned; and calculating the values of said measurement parameters from said positions.

2. The method according to claim 1, wherein the positions of the tangential horizontal and vertical straight lines are determined at an inside contour of each half-frame on said image and which further comprises extracting a contour of said frame from said image.

3. A method according to claim 1, which comprises the steps of:

supplying at least a real contour of said frame, and the angles of inclination of said frame;

calculating, as a function of said angles of inclination, a projection of said real contour on said image;

comparing said projection with the contours extracted from said image by sweeping said projection over said image and calculating therefrom, for each position of said projection, the correlation between said projection and said contours extracted from said image;

determining the positions of the horizontal and vertical straight lines tangential to said frame, using the position of said projection for which said correlation is at a maximum.

4. A method according to claim 3, wherein the step of calculating the values of said measurement parameters from said positions is achieved by comparing the relative positions of the centers of the pupils of the eyes of said spectacle wearer and the straight lines tangential to the inside contours of said frame.

5. A method according to claim 1 which further comprises defining contours of the frame using the position measurements associated with the horizontal and vertical lines which are tangential to the frame.

6. A method for determining measurement parameters for a spectacle wearer comprising the steps of:

generating an image of a spectacle wearer provided with a spectacle frame;

determining automatically, on said image, by luminance gradient analysis, where a plurality of horizontal and vertical straight lines tangential to said frame would be positioned;

determining automatically, on said image, by luminance gradient analysis, where the center of each pupil of the eyes of said wearer would be positioned;

defining four windows of predetermined size around the center of each pupil, each window containing one straight line tangential to an inside contour of each half-frame; and calculating the values of said measurement parameters from said positions.

7. A method according to claim 6, wherein the step of determining the positions of the horizontal and vertical straight lines tangential to said frame comprises the steps, within each of said windows, of:

determining, within said window, those points on the image for which the norm of the luminance gradient is higher than a threshold value in order to obtain the inside and outside contours of said frame within said window;

determining the shape of said frame within said window, from said contours;

determining, as a function of said window, a tangent to the inside contour of said frame.

8. A method according to claim 7, wherein said threshold value is selected whereby a predetermined number of said points on the image have a value of the norm of their luminance gradient above said threshold value.

9. A method according to claim 8, which includes a step of calculating angles of inclination comprising the steps of:

supplying at least a real contour of said frame;

calculating, for the various possible values of angles of inclination, a projection of said real contour on said image;

comparing said projection with the contours extracted from said image by calculating, for said values of angles of inclination, the correlation between said projection and said contours extracted from said image;

the values of said angles of inclination being those values for which said correlation is at a maximum.

10. A method according to claim 9, which further comprises the steps of:

supplying at least a real contour of said frame, and the angles of inclination of said frame;

calculating, as a function of said angles of inclination, the projection of said real contour on said image;

comparing said projection with the contours extracted from said image by sweeping said projection over said image and calculating therefrom, for each position of said projection, the correlation between said projection and said contours extracted from said image;

determining the positions of the horizontal and vertical straight lines tangential to said frame, using the position of said projection for which said correlation is at a maximum.

11. A method according to claim 10, wherein the step of calculating the values of said measurement parameters from said positions is achieved by comparing the relative positions of the centers of the pupils of the eyes of said spectacle wearer and the straight lines tangential to the inside contours of said frame.

12. A method according to claim 6 which further comprises defining contours of the frame using the position measurements associated with the horizontal and vertical lines which are tangential to the frame.

13. A method for determining measurement parameters for a spectacle wearer comprising the steps of:

generating an image of a spectacle wearer provided with a spectacle frame;

determining automatically, on said image, by luminance gradient analysis, where a plurality of horizontal and vertical straight lines tangential to said frame would be positioned;

determining automatically, on said image, by luminance gradient analysis, where the center of each pupil of the eyes of said wearer would be positioned by:
determining a window covering the region of the pupil;
determining, within said window, those points on the image having a luminance that is higher than a threshold value; and
calculating the position of the centroid of said points; and calculating the values of said measurement parameters from said positions.

14. A method according to claim 13, wherein the step of determining said window is done by seeking, in the region of each pupil, that point in the image for which a norm of the gradient is a maximum, and then centering a window of a predetermined size on said point.

15. A method according to claim 14, which includes a step of defining four windows of predetermined size around the position of the center of each pupil, each containing one straight line tangential to the inside contour of each half-frame.

16. A method according to claim 15, wherein the step of determining the positions of the horizontal and vertical straight lines tangential to said frame automatically comprises the steps, within each of said windows, of:

determining, within said window, those points on the image for which the norm of the luminance gradient is higher than the threshold value in order to obtain the inside and outside contours of said frame within said window;

determining the shape of said frame within said window, from said contours;

determining, as a function of said window, the tangent to the inside contour of said frame.

17. A method according to claim 16, wherein said threshold value is selected whereby a predetermined number of said points on the image have a value of the norm of their luminance gradient above said threshold value.

18. A method according to claim 17, which includes a step of calculating angles of inclination comprising the steps of:

supplying at least a real contour of said frame;

calculating, for the various possible values of angles of inclination, a projection of said real contour on said image;

comparing said projection with the contours extracted from said image by calculating, for said values of angles of inclination, the correlation between said projection and said contours extracted from said image;

the values of said angles of inclination being those values for which said correlation is at a maximum.

19. A method according to claim 18, which comprises the steps of:

supplying at least a real contour of said frame, and the angles of inclination of said frame;

calculating, as a function of said angles of inclination, the projection of said real contour on said image;

comparing said projection with the contours extracted from said image by sweeping said projection over said image and calculating therefrom, for each position of said projection, the correlation between said projection and said contours extracted from said image;

determining the positions of the horizontal and vertical straight lines tangential to said frame, using the position of said projection for which said correlation is at a maximum.

20. A method according to claim 19, wherein the step of calculating the values of said measurement parameters from said positions is achieved by comparing the relative positions of the centers of the pupils of the eyes of said spectacle wearer and the straight lines tangential to the inside contours of said frame.

* * * * *